United States Patent [19]
Horino et al.

[11] Patent Number: 5,968,529
[45] Date of Patent: Oct. 19, 1999

[54] DISPERSION OF ULTRAVIOLET INTERCEPTING MOISTURE-RETAINING AGENT AND COSMETIC ARTICLE INCORPORATING THE DISPERSION

[75] Inventors: Masaakira Horino, Kanagawa; Miwa Nishizawa, Saitama, both of Japan

[73] Assignee: Miyoshi Kasei, Inc., Saitama, Japan

[21] Appl. No.: 08/886,895

[22] Filed: Jul. 2, 1997

[30] Foreign Application Priority Data

Jul. 5, 1996 [JP] Japan .................................. 8-195646
Aug. 7, 1996 [JP] Japan .................................. 8-224367

[51] Int. Cl.$^6$ .............................. A61K 7/00; A61K 7/42
[52] U.S. Cl. .......................... 424/401; 424/59; 424/60; 424/400
[58] Field of Search ......................... 424/89, 60, 400, 424/401

[56] References Cited

U.S. PATENT DOCUMENTS 4,332,354   6/1982   deMonterey et al. .................... 241/16
5,091,013   2/1992   Miyoshi et al. ........................ 106/505

FOREIGN PATENT DOCUMENTS 1022621   3/1966   United Kingdom .
2260129   4/1993   United Kingdom .

*Primary Examiner*—Shelley A. Dodson
*Attorney, Agent, or Firm*—Armstrong, Westerman, Hattori, McLeland & Naughton

[57] ABSTRACT

A dispersion of a moisture-retaining agent for use in a cosmetic article is disclosed which is characterized by having dispersed in the moisture-retaining agent an inorganic ultraviolet intercepting material having the molecules of the moisture-retaining agent adsorbed thereon by a mechanochemical reaction. This dispersion manifests an excellent ability to disperse the inorganic ultraviolet intercepting material, affords a highly effective protection against ultraviolet light, and exhibits excellent stability in a cosmetic article.

A cosmetic article containing the dispersion is also disclosed.

15 Claims, No Drawings

DISPERSION OF ULTRAVIOLET INTERCEPTING MOISTURE-RETAINING AGENT AND COSMETIC ARTICLE INCORPORATING THE DISPERSION

BACKGROUND OF THE INVENTION

1. Field of the Invention

This invention relates to a dispersion of a moisture-retaining agent for use in a cosmetic article and a cosmetic article containing the dispersion, and more particularly to a dispersion of a moisture-retaining agent for use in a cosmetic article which manifests an excellent ability to disperse an inorganic ultraviolet intercepting material, affords a highly effective protection against ultraviolet light, and exhibits excellent stability in a cosmetic article and a cosmetic article containing the dispersion. The invention further relates to a dispersion of a moisture-retaining agent which contributes to simplify the production of a cosmetic article.

2. Description of the Prior Art

It has been heretofore known that the ultraviolet light produces various adverse effects on the skin. The ultraviolet light is divided into a long-wave ultraviolet light (UV-A wave), 400–320 nm in wavelength, a medium-wave ultraviolet light (UV-B wave), 320–290 nm in wavelength, and an ultraviolet light (UV-C wave), not more than 290 nm in wavelength.

The UV-C wave is absorbed in the ozonosphere and sparingly allowed to reach the earth's surface. The UV-B wave reaching the earth's surface, when suffered to impinge in a quantity exceeding a certain level on the skin, forms erythema and blisters in the skin and promotes the formation of melanin. Then, it is held that the UV-A wave very weakly induces erythema as compared with the UV-B wave and blackens the skin without substantially entraining erythema. Further, it profusely permeates the skin, promotes the cross-linkage of collagen which is a protein in the skin, degrades the elasticity and the water-retaining power of the collagen, induces the formation of wrinkles, constitutes a cause for liver spots and melanotic freckles, and brings about the aging of the skin. It is also known that the UV-A wave augments the peroxide lipid in the dermal tissue and consequently constitutes a cause for cancer of the skin.

Various cosmetic articles incorporating therein ultraviolet absorbents have been heretofore developed and marketed for the purpose of protecting the skin against such troubles as are ascribable to the ultraviolet light. For these cosmetic articles, such synthetic ultraviolet absorbents as benzophenones, aminobenzoic acids, cinnamic esters, benzotriazoles, salicyls, and dibenzoyl methanes and minute particles of such inorganic pigments as titanium oxide, zinc oxide, and iron oxide are used.

SUMMARY OF THE INVENTION

In the course of the present invention the following problems have been found.

Superfine titanium dioxide particles which have individual particle diameters thereof defined within 10–50 nm are characterized by possessing the most powerful physiological action, randomly reflecting the ultraviolet light, 290–320 nm in wavelength, which inflicts erythema and inflammation on the skin, and generously passing the visible light. The minute particles of titanium dioxide which are available on the market, however, generate a powerful cohesive force between the individual particles on account of strong surface activity and by virtue of the minute amount of water adsorbed thereon. The particles of such a size as manifests the optical property of light scattering suffer the scattering in the Rayleigh region and the scattering in the Mie region to manifest their action centrally and induce substantial degradation of the sensation of transparency. A cosmetic article which incorporates therein superfine titanium dioxide particles, therefore, is at a disadvantage in suffering the film of the cosmetic article spread on the skin to emit a bluish white color prominently and also suffering the strong surface activity of the superfine titanium dioxide particles to induce gradual cohesion of the particles mechanically dispersed in the cosmetic article with the elapse of time possibly to the extent of lowering the value of SPF (sun protection factor) and rendering it difficult to attain the expected effective protection of the skin against the ultraviolet light as expected.

When superfine titanium dioxide particles taken individually have an average particle diameter of 0.01–0.09 $\mu$m, they as an aggregate have an average particle diameter of 1.2–5.0 $\mu$m (as determined by the laser method). These particles retain strong active points. When they are irradiated with the ultraviolet light, therefore, they decompose the adsorbed water and generate OH and OH$_2$ free radicals which have very strong oxidizing power. These free radicals discolor and fade the tar pigment legally designated for use in cosmetic articles or degenerate standard oils allowed for cosmetic articles.

The superfine titanium dioxide particles in the untreated form have three to four times as high potency as fine zinc oxide particles in terms of the effect in protecting the skin against the ultraviolet light and, therefore, are useful for exalting the value of SPF. It is problematic, however, to incorporate them in a cosmetic article in the expectation of exalting the value of SPF because the film of the cosmetic article spread on the skin emits a bluish white color and consequently impairs the effect of beautification aimed at. Further, the strong surface activity possessed by the superfine particles constitutes a cause for inducing gradual cohesion of the dispersed particles with the elapse of time and lowering the value of SPF.

Zinc oxide has a strong surface activity and forms strong cohesion between the fine particles thereof. This surface activity, judging from the degree of fading of the legal pigment, appears to be about five times as high as that of superfine titanium dioxide particles. Further, zinc oxide has a strong catalytic activity and, therefore, is at a disadvantage in inducing the oil in the cosmetic article to decompose with emission of offensive odor.

Particularly, the emulsion uses a thickening agent for the purpose of acquiring an appropriate degree of viscosity. Since zinc oxide has a strong surface activity, it is at a disadvantage in yielding to agglomeration together with the thickener, upsetting the expectation for the effective protection of the skin against the ultraviolet light, and harming the stability of the emulsion itself. Further, the emulsion composition using a synthetic ultraviolet absorbent in combination with zinc oxide is at a disadvantage in suffering gradual precipitation and consequent persistence of light yellow to light orange crystals with the elapse of time in the presence of a trace quantity of iron or oxide ions or in the presence of zinc oxide, suffering coloration of the emulsion itself, and impairing the commercial value of the composition on account of the impaired appearance.

In the cosmetic article industry, the trend of lowering the production cost has been gaining in impetus and the conservation of labor in the production process of the cosmetic article has been constituting an important task. Since the effective protection of the skin against the ultraviolet light forms the basic need on the part of consumers, the need of the cosmetic article maker to procure a dispersion having such inorganic ultraviolet intercepting materials as superfine titanium dioxide particles, superfine zinc oxide particles, and minute zinc oxide particles incorporated as dispersed therein, namely the need to simplify the process of production by obtaining direct use of the dispersion instead of pulverizing the inorganic materials and dispersing the resultant powder, has been finding growing recognition.

Among the dispersions introduced heretofore to the market under these circumstances are included those which use trimethyl siloxysuccinic acid as a dispersant and have superfine titanium dioxide particles and superfine zinc oxide particles dispersed in silicone oil. These dispersions themselves are stable. Such a dispersion, however, is at a disadvantage in succumbing to agglomeration caused by a thickener when it is incorporated in an emulsion, failing to attain the value of SPF or the value of PFA (the index for designating the cut of UVA) aimed at, and impairing the stability of the emulsion incorporating the dispersion., Incidentally, the value of PFA is a value of the sort determinable by the use of an SPF analyzer (produced by Optometrics Corp. and marketed under trademark designation of "SPF-290 Analyzer"). The ease with which the dispersion passes the ultraviolet light decreases in accordance as the value of PFA increases.

The aqueous dispersion which uses polysodium acrylate as a dispersant and has superfine titanium dioxide particles dispersed in water is at a disadvantage in failing to fulfill the function as a dispersant because the polysodium acrylate reacts with the moisture-retaining agent used in the cosmetic article and separates in the form of thick malt syrup from the dispersion.

The first object of this invention is to provide a novel dispersion of a moisture-retaining agent for use in a cosmetic article unlike the conventional equivalent mentioned above and a cosmetic article containing the dispersion.

The second object of this invention is to solve the problems attendant on the prior art as mentioned above and provide a dispersion of a moisture-retaining agent excelling in the ability to disperse an inorganic ultraviolet intercepting material, restraining high optical activity and catalytic activity of the inorganic ultraviolet intercepting material, enjoying excellent stability in a cosmetic material, and imparting preeminently excellent ultraviolet intercepting function and, furthermore, allowing itself to be incorporated at a high degree of dispersion in a cosmetic article by a simple procedure and a cosmetic article containing the dispersion.

DETAILED DESCRIPTION OF THE INVENTION

In view of the true state of the prior art mentioned above, the present inventors have made various studies on inorganic ultraviolet intercepting materials in search of a mode for enabling these materials to manifest perfectly their inherent ability to intercept the, ultraviolet light. As a result, they have found that a composition of the mode which is obtained by preparatorily applying a powerful shearing force on an inorganic ultraviolet intercepting material and a dispersant capable of aiding in dispersing the material mentioned above (or the combination of the two members mentioned above plus a fixating agent for fixing these members) thereby forming a mixture having undergone the steps of adsorption and dispersion of material particles effected by the resultant mechanochemical reaction and then uniformly dispersing this mixture in a moisture-retaining agent solves all the problems attendant on the prior art, exalts the stability of a system which incorporates the composition and, in addition, expels such drawbacks of the conventional inorganic ultraviolet intercepting material as inferior adhesiveness and expansibility which are manifested when the cosmetic article using the material is applied in the form of a uniform film on the skin, and manifests an effect not attainable by the prior art. This invention has been perfected as a result.

Specifically, this invention accomplishes the objects mentioned above by providing the following dispersion of a moisture-retaining agent and a cosmetic article containing the dispersion.

(1) A dispersion of a moisture-retaining agent characterized by having dispersed in a moisture-retaining agent an inorganic ultraviolet intercepting material having the molecules of the moisture-retaining agent adsorbed thereon by a mechanochemical reaction.

(2) A cosmetic article containing the dispersion of a moisture-retaining agent.

The dispersion of a moisture-retaining agent and the cosmetic article containing this dispersion according to this invention as described above do not essentially require either the dispersant or the fixating agent mentioned above. A dispersion of the mode which is obtained by preparatorily applying a powerful shearing force on an inorganic ultraviolet intercepting material and a moisture-retaining agent in the absence of the dispersant and the fixating agent mentioned above thereby forming a mixture; having undergone the steps of adsorption and dispersion of material particles effected by the resultant mechanochemical reaction and then uniformly dispersing this mixture in a moisture-retaining agent solves all the problems attendant on the prior art, exalts the stability of a system which incorporates the composition and, in addition, expels such drawbacks of the conventional inorganic ultraviolet intercepting material as inferior adhesiveness and expansibility which are manifested when the cosmetic article using the material is applied in the form of a uniform film on the skin.

The dispersion of a moisture-retaining agent mentioned above is preferred to be embodied as follows.

The dispersion further incorporates therein a dispersant capable of aiding in the dispersion of the inorganic ultraviolet intercepting material.

The dispersion has the inorganic ultraviolet intercepting material fixed on a fixating agent capable of fixing an inorganic ultraviolet intercepting material.

The inorganic ultraviolet intercepting material, the dispersant, and the moisture-retaining agent (including the molecules of the moisture-retaining agent adsorbed on the inorganic ultraviolet intercepting material) are present in the dispersion in the gravimetric ratio of 1:0.2–0.9:2–9.5.

The inorganic ultraviolet intercepting material, the fixating agent, the dispersant, and the moisture-retaining agent (including the molecules of the moisture-retaining agent adsorbed on the inorganic ultraviolet intercepting material) are present in the dispersion in the gravimetric ratio of 1:0.4–0.9:0.2–0.6:2–9.5.

The dispersion contains the inorganic ultraviolet intercepting material in an amount of not less than 9.5% by weight.

The dispersion contains the inorganic ultraviolet intercepting material in an amount in the range of 20–50% by weight and the moisture-retaining agent (including the molecules of the moisture-retaining agent adsorbed on the inorganic ultraviolet intercepting material) in an amount in the range of 50–80% by weight.

The cosmetic article preferably contains the dispersion of a moisture-retaining agent in an amount in the range of 3.5–80% by weight.

The cosmetic article preferably contains the dispersion of a moisture-retaining agent [comprising 20–50% by weight of the inorganic ultraviolet intercepting material and 50–80% by weight of the moisture-retaining agent (including the molecules of the moisture-retaining agent adsorbed on the inorganic ultraviolet intercepting material)] in an amount in the range of 0.5–80% by weight.

The ranges of numerical values described in this invention shall be construed as including not only the numerical values constituting the opposite terminals of the ranges but also all the intermediate values embraced within the terminals.

Dispersion of Moisture-Retaining Agent

The dispersion of a moisture-retaining agent has dispersed in a moisture-retaining agent an inorganic ultraviolet intercepting material having the molecules of the moisture-retaining agent adsorbed thereon by a mechanochemical reaction.

The inorganic ultraviolet intercepting material to be used in this invention is inorganic oxide, preferably superfine or minute inorganic oxide or hydrated oxide particles. As concrete examples oil this material, titanium dioxide, iron-containing titanium dioxide (the iron content thereof preferably in the range of 1–30% by weight, based on the weight of $TiO_2$), zinc oxide, zirconium oxide, cerium oxide, and iron oxide may be cited. For the purpose of improving this material in compatibility with the dispersant and weatherability as well, the particles of this material may be coated with the oxide or hydroxide of aluminum, titanium, zirconium, silicon, or tin. One or the mixture thereof may be used therefore.

When the inorganic ultraviolet intercepting material to be used for this invention happens to be titanium dioxide, the average single particle diameter is preferably in the range of 0.01–5.0 μm (in the case of particles shaped like a spindle, the minor axis in the range of 0.01–0.03 μm and the major axis in the range of 0.05–0.1 μm), the specific surface area in the range of 25–120 $m^2$/g (determined by the simplified BET method), and the oil absorbing capacity in the range of 17–60.

When the inorganic ultraviolet intercepting material happens to be zinc oxide, it may be manufactured by any of the known methods such as the French method, the American method, and the wet method. The zinc oxide thus produced proves preferably when the average single particle diameter falls in the range of 0.01–0.60 μm (determined by the air passage method), the specific gravity in the range of 5.4–5.6, the refractive index in the range of 1.9–2.0, and the specific surface area in the range of 4.0–80 $m^2$/g (determined by the BET method).

The fixating agent to be used in this invention is only required to be capable of fixing the inorganic ultraviolet intercepting material. As concrete examples of the fixating agent which proves appropriate, the family of illites such as sericite, common mica, black mica, lithia mica, and synthetic mica, the family of kaolins such as kaolinite, nakhlite, dekkito, and halloycite, the family of sillimanites such as fibrolite and kyanite, and the family of magnesium silicates such as talc and serpentine may be cited.

The preferred average particle diameter of the fixating agent is 0.2–20 μm (determined by the laser diffraction method using an apparatus made of Horiba, Ltd.) and the preferred average thickness of the fixating agent is 0.01–3.0 μm (determined by the method which comprises embedding a sample in resin and observing a slice of the embedded sample under SEM).

The dispersant to be used in this invention is only required to be capable of aiding in the dispersion of the inorganic ultraviolet intercepting material in the moisture-retaining agent. Examples are sheet silicates and clayish minerals belonging to the family of smectites. As concrete examples of the dispersant usable herein, montmorillonite, bentonite, beidellite, nontronite, saponite, and hectorite may be cited. These may be natural products or synthetic products. Such commercially available dispersants as KUNIPIA (produced by Kunimine Industries Co., Ltd.), LAPONITE (produced by Laporte Industries Ltd.), SUMECTON (produced by Kunimine Industries Co. Ltd.), fluorine tetrasilicate mica (Topy Industries Ltd.), VEEGUM (produced by VANDER-VILT Co., Inc.), and microcrystalline cellulose (produced by Asahikasei Industries Co., Ltd., "ABCICEL RC 591") are also usable.

The moisture-retaining agent to be used in this invention may be any of the various humidity-retaining agents which are usable for incorporation in cosmetic articles. As concrete examples of the moisture-retaining agent usable herein, 1,3-butylene glycol, propylene,glycol, dipropylene glycol, glycerin, polyethylene glycol, diglycerin, erythritol, pentaerythritol, hexylene glycol, xylytol, sorbitol, maltitol, mannitol, triglycerin, tetraglycerin, maltotriose, glucose, fructose, sucrose, amylolytic maltose, chondroitin sulfuric acid, hyaruloitic acid, mucoitin sulfuric acid, charonic acid, athero collagen, sodium lactate, bile salt, d,1-pyrrolidone carboxylates, extract of rose, extract of milfoil, pentaglycerin, hexaglycerin, tetraglycerin, octaglycerin, nonaglycerin, and decaglycerin may be cited. A solid moisture-retaining agent is preferably used as dissolved in such a solvent as water.

The gravimetric ratio of the inorganic ultraviolet intercepting material, the fixating agent, the dispersant, and the moisture-retaining agent in the dispersion of a moisture-retaining agent is, preferably in the range of 1:0.4–0.9:0.2–0.6:2–9.5. The gravimetric ratio of the inorganic ultraviolet intercepting material, the dispersant, and the moisture-retaining agent is, preferably in the range of 1:0.2–0.9:2–9.5. When the dispersion of the moisture-retaining agent of this invention contains neither the fixating agent nor the dispersant, the gravimetric ratio of the inorganic ultraviolet intercepting material and the moisture-retaining agent is in the range of 1:2–9.5 (approximately 9.5–33% by weight as converted to the content of the inorganic ultraviolet intercepting material).

Further, when the dispersion of the moisture-retaining agent of this invention contains neither the fixating agent nor the dispersant, the content of the inorganic ultraviolet intercepting material in the dispersion of the moisture-retaining agent may be set in the range of 20–50% by weight, preferably 30–48% by weight, and more preferably 40–45% by weight. When the concentration of the inorganic ultraviolet intercepting material in the dispersion of the moisture-retaining agent is set at or above 20% by weight, the dispersion of the moisture-retaining agent is not required to be incorporated at a high concentration in the cosmetic article for the purpose of enabling the produced cosmetic article to acquire a high value of SPF or a high value of PFA. Thus, the restriction in terms of the composition and the restriction in terms of the sensation of the cosmetic article used on the skin can be allayed. When the concentration mentioned above is set at or below 50% by weight, the dispersion of the moisture-retaining agent tends to assume a pasty state, enjoys perfect workability in the process of preparation thereof, and allows the inorganic ultraviolet intercepting material to be dispersed smoothly therein.

Next, an example of the production of the dispersion of the moisture-retaining agent will be described below. The dispersion of the moisture-retaining agent is manufactured by premixing the dispersant, the fixating agent, and the inorganic ultraviolet intercepting material in a mixing device or a mixing•dispersing device such as, for example, the Henschel mixer, the NAUTAA mixer, or the V-shaped blender, then optionally pulverizing the resultant mixture with a shock type pulverizer (such as, for example, a BANDAMU mill or a pulverizer), then stirring the mixture with a shaking ball mill or a pebble mill to ensure more thorough dispersion of the particles of the inorganic ultraviolet intercepting material, and promoting the fixation of the particles on the fixating agent and the dispersant by utilizing the mechanochemical reaction of one sort capable of fixing part of the particles on the surfaces of the fixating agent and the dispersant. The steps mentioned above are not necessary where the dispersant and the fixating agent are not used.

The inorganic ultraviolet intercepting material powder which has or has not undergone the treatment and the moisture-retaining agent added thereto are treated together with a dispersing device such as, for example, a sand mill, a shaking ball mill, a pebble mill, a disc mill, an attriter, a dyno-mill, a KOBORU mill, an ONGU mill, or a basket mill thereby dispersing the inorganic ultraviolet intercepting material and consequently obtaining the dispersion of the moisture-retaining agent.

In the process for the production of the dispersion of the moisture-retaining agent, the selection of the kind of dispersing device, the selection of the medium for pulverization and dispersion, and the selection of the optimum conditions of pulverization and dispersion are important for the preparation of the dispersion of the moisture-retaining agent of high quality. For the horizontal or vertical sand mill, for example, zirconia beads which have a high absolute specific gravity, high rigidity, and high wear resistance are preferably used as the medium. Appropriately, the zirconia beads have a diameter of 0.5 mm.

When a ball mill is used, for example, the vessel and the beads of this ball mill are preferred to be made of a zirconia material or an alumina material in due consideration of the importance of preventing the ball mill from being defiled with chips arising from the abrasion and improving the efficiency of dispersion. For the sake of the efficiency of dispersion, the amount of the material to be placed in the ball mill is preferred to be such that the balls used in the mill may be wholly immersed in the total volume of the raw materials for the dispersion of the moisture-retaining agent. As concerns the size of the balls to be used, it is more advantageous for the sake of exalting the efficiency of dispersion to use a mixture of balls having different diameters than to use a collection of balls of one equal diameter.

Since the dispersion of the moisture-retaining agent which has been manufactured under conditions highly appropriate for the dispersion of the inorganic ultraviolet intercepting material is incorporated in a given system, the ultraviolet intercepting function inherently possessed by the dispersion can be thoroughly manifested. By the usual method of compounding the powder (the powder of such raw materials as the inorganic ultraviolet intercepting material which form the dispersion of moisture-retaining agent of this invention) with a given cosmetic article, numerous clusters of the inorganic ultraviolet intercepting material are scattered and they obstruct the manifestation of the ultraviolet intercepting function as hoped for and, on account of the persistence of strong active points, the legally allowed tar pigment used in the cosmetic article is discolored or faded on exposure to the ultraviolet light and the oil agent used in the cosmetic article is likewise discolored or faded. When the powder of the inorganic ultraviolet intercepting material and other raw materials is compounded in the cosmetic article by the usual method, the inorganic ultraviolet intercepting material is readily agglomerated by aging on account of the strong surface activity thereof and the value of SPF is inevitably lowered in spite of powerful temporary dispersion by the use of a disperser or homomixer.

The stabilization of dispersion for the dispersion of the moisture retaining agent and the cosmetic article containing this dispersion will be described below. Superfine titanium dioxide particles and superfine zinc oxide particles are used herein as the inorganic ultraviolet intercepting material.

(1) As concerns the dispersion of superfine titanium dioxide particles and superfine zinc oxide particles in the dispersion of the moisture-retaining agent, the state in which superfine titanium dioxide particles and superfine zinc oxide particles are dispersed as fixed on the surface of the fixating agent, the state in which the superfine zinc oxide particles are dispersed, and the state in which the superfine titanium dioxide particles are conceivable.

Firstly, in the case of having the superfine titanium dioxide particles and the superfine zinc oxide particles dispersed as fixed on the surface of the fixating agent, the surface of the fixating agent assumes a (−) electric charge and the superfine zinc oxide particles assume a (+) electric charge. Since the superfine titanium dioxide particles combine the qualities of a solid acid and a solid base, it is thought that they are acted on by an electric charge opposite that acting on the solid surface and are fixed during the process of a mechanochemical reaction. The surface of the particles thus produced has an excess (+) charge of the superfine zinc oxide particles relative to the (−) charge of the fixating agent and the moisture-retaining agent is adsorbed by the interaction of the charge with the moisture-retaining agent.

Secondly, the superfine zinc oxide particles have a (+) surface charge and adsorb the moisture-retaining agent through the mutual attraction of the (+) charge thereof with the (−) charge of the moisture-retaining agent. Thirdly, since the superfine titanium dioxide particles combine the qualities of acid points and base points, it is inferred that they interact with the moisture-retaining agent and consequently adsorb it. In short, since the moisture-retaining agent is adsorbed on the surface of the particles of the inorganic ultraviolet intercepting material, the particles are prevented from agglomerating and consequently the stabilization of dispersion is accomplished.

It is inferred that in the presence of the dispersion, the particles of the inorganic ultraviolet intercepting material are intertwined either linearly or in a complicated manner or the clayish mineral of the family of smectite assumes a structural viscosity of the nature of thixotropy and, consequently, the sedimentation of the particles and the separation of the particles from the moisture-retaining agent are restrained.

As concerns the stabilization of the dispersion in the cosmetic article, the ordinary method of emulsification attains the emulsification by causing the moisture-retaining agent to wet a thickening agent and adding purified water to the mixture. In this case, the superfine titanium dioxide particles and the superfine zinc oxide particles which have a particularly strong surface activity react with the thickening agent and form an aggregate. When sodium carboxymethyl cellulose as a thickening agent is placed in an aqueous solution, the Na departs from the compound and forms a Na cation and consequently the aqueous solution manifests alkalinity and the cellulose proper assumes a (−) electric charge. Thus, the cellulose proper tends to react with the superfine titanium dioxide particles and the superfine zinc oxide particles which are positively charged.

In contrast, the dispersion of the moisture-retaining agent of this invention manifests a high value of SPF probably because the particles of the moisture-retaining agent exhibit a barrier effect for the cellulose proper assuming a (−) electric charge and prevent the reaction thereof with the inorganic ultraviolet intercepting material even when the moisture-retaining agent is adsorbed to the inorganic ultraviolet intercepting material and sodium carboxymethyl cellulose as a thickening agent approximates closely to the material.

(2) When the state in which the superfine titanium dioxide particles and the minute zinc oxide particles are dispersed in the dispersion of a moisture-retaining agent in the absence of the fixating agent and the dispersant is assumed, it is inferred that the moisture-retaining agent is dispersed as strongly adsorbed by the mechanochemical reaction to the inorganic ultraviolet intercepting material.

This dispersion of the moisture-retaining agent is made to expose through the surface thereof a lattice defect, an ionized part, and a fractured part of bondage when the inorganic ultraviolet intercepting material and the moisture-retaining agent are exposed to powerful shearing force to attrite the surface of the inorganic ultraviolet intercepting material and pulverize the particles of the materials mentioned above during the process of manufacture of the dispersion. Though the minute zinc oxide particles have a lower surface activity than the superfine zinc oxide particles, they are enabled to have the surface activity thereof notably heightened when they are exposed to the mechanochemical reaction in the manner described above. Since the minute zinc oxide particles consequently assume a strong surface (+) electric charge, the functional group of the moisture-retaining agent such as, for example, the OH group assuming ($\delta^-$) approaches the part of the surface (+) charge and forms an electric bondage therewith and the moisture-retaining agent is integrated with the minute zinc oxide particles and the moisture-retaining agent is strongly adsorbed to the dangling bond arising from the pulverization of the minute zinc oxide particles. It is, therefore, inferred that the surface of the zinc oxide functions as an electrical double-layer film of a sort. The superfine titanium dioxide particles, similarly on account of the attrition of the surface thereof, have the surface activity thereof exalted and, at the same time, combine both a solid acid and a base point and, therefore, interact with the moisture-retaining agent and presumably accomplish the stabilization of dispersion due to strong adsorption of the moisture-retaining agent.

When the inorganic ultraviolet intercepting material is dispersed in a high concentration in the moisture-retaining agent, it is inferred that the sedimentation of the particles and the separation of the particles from the moisture-retaining agent are repressed on account of the viscosity of the moisture-retaining agent itself, the high voluminal concentration of the inorganic ultraviolet intercepting material, and the structural viscosity consequently induced.

As concerns the stabilization of the dispersion in the cosmetic article, the ordinary method of emulsification attains the emulsification by causing the moisture-retaining agent to wet a thickening agent and adding purified water to the mixture. In this case, the superfine titanium dioxide particles and the superfine zinc oxide particles which have a particularly strong surface activity react with the thickening agent and form an aggregate. When sodium carboxymethyl cellulose as a thickening agent is placed in an aqueous solution, the Na departs from the compound and forms a Na cation and consequently the aqueous solution manifests alkalinity and the cellulose proper assumes a (−) electric charge. Thus, the cellulose proper tends to react with the superfine titanium dioxide particles and the superfine zinc oxide particles which are positively charged.

In contrast, the dispersion of the moisture-retaining agent of this invention manifests a high value of SPF probably because the particles of the moisture-retaining agent exhibit a barrier effect for the cellulose proper assuming a (−) electric charge and prevent the reaction thereof with the inorganic ultraviolet intercepting material even when the moisture-retaining agent is adsorbed to the inorganic ultraviolet intercepting material and sodium carboxymethyl cellulose as a thickening agent approximates closely to the material.

The superfine titanium dioxide particles and the superfine zinc oxide particles, especially the latter, have a very strong surface activity. When an organic ultraviolet absorbent is incorporated in the composition, the catalytic activity originating in the surface activity of the inorganic ultraviolet intercepting material and the free radical generated by the material discolor the organic ultraviolet absorbent and discolor the cosmetic material to yellow-orange color and degenerate it and prevent the organic ultraviolet absorbent from fulfilling the function inherent therein. Further, the ion partly dissociated from the surface of the inorganic ultraviolet intercepting material reacts with the organic ultraviolet absorbent and gives rise to a colored precipitate and the strong surface charge of the ion arising from the partial dissociation reacts with the organic ultraviolet absorbent and gives birth to a precipitate and these precipitates both go to deprive the organic ultraviolet absorbent wholly of the function thereof.

It is inferred that the dispersion of the moisture-retaining agent of this invention exhibits a high value of SPF and a high value of PFA because the moisture-retaining agent is strongly adsorbed to the inorganic ultraviolet intercepting material and caused to occlude the active points of the inorganic ultraviolet intercepting material in consequence of the mechanochemical reaction and, moreover, the moisture-retaining agent fulfills the role of an electric double layer of a sort and consequently prevents itself from reacting with the inorganic ultraviolet intercepting material.

Cosmetic Article

The cosmetic article of this invention contains the dispersion of the moisture-retaining agent of this invention. The content of the dispersion of the moisture-retaining agent of this invention is usually in the range of, preferably 3.5–80% by weight, more preferably 7.0–70% by weight, based on the total weight of the cosmetic article. If the content is less than 3.5% by weight, the cosmetic article will be liable neither to prevent the sunlight from drying and inflaming the skin or causing the skin to sustain sedimentation nor to protect the skin against decline of the function thereof. If the content exceeds 80% by weight, the excess will neither do any good economically nor add proportionately to the effect in intercepting the ultraviolet light and, at the same time, the cosmetic article will manifest poor spreadability and the uniform film thereof will betray deficiency in adhesiveness and fastness of contact and offer no lasting effect in intercepting the ultraviolet light. The cosmetic article, when necessary, may additionally incorporate therein an ultraviolet absorbent to augment the value of SPF and the value of PFA by virtue of the light scattering power of the inorganic ultraviolet intercepting material and the synergistic action of the organic ultraviolet absorbent.

When the cosmetic article contains the dispersion of the moisture-retaining agent which contains neither the fixating agent nor the dispersant, it is possible to enlarge the range of the content ratio of the dispersion of the moisture-retaining agent. The content of the dispersion is usually in the range of, preferably 0.5–80% by weight, more preferably 7.0–70% by weight based on the total weight of the cosmetic article. If the content is less than 0.5% by weight, the cosmetic article will be liable neither to prevent the sunlight from drying and inflaming the skin or causing the skin to sustain sedimentation nor to protect the skin against decline of the function thereof. If the content exceeds 80% by weight, the excess will neither do any good economically nor add proportionately to the effect in intercepting the ultraviolet light and, at the same time, the cosmetic article will manifest poor spreadability and the uniform film thereof will betray deficiency in adhesiveness and fastness of contact and offer no lasting effect in intercepting the ultraviolet light. The cosmetic article, when necessary, may additionally incorporate therein an ultraviolet absorbent to augment the value of SPF and the value of PFA by virtue of the light scattering power of the inorganic ultraviolet intercepting material and the synergistic action of the organic ultraviolet absorbent.

The organic ultraviolet absorbent to be used in the present invention may be any of the conventional equivalents accepted for use in the cosmetic articles. Now, typical compounds usable as the organic ultraviolet absorbent herein will be cited below.

(1) Benzoic Acid Type Ultraviolet Absorbents

Para-aminobenzoic acid, para-aminobenzoic acid monoglycerin, N,N-dipropoxy ethyl para-aminobenzoate, N,N-diethoxy ethyl para-aminobenzoate, N,N-dimethyl amyl para-aminobenzoate, N,N-dimethyl octyl para-aminobenzoate, N,N-dimethyl butyl para-aminobenzoate, etc.

(2) Anthranilic Acid Type Ultraviolet Absorbents

Homomenthyl N-N-acetyl anthranilate, etc.

(3) Salicylic Acid Type Ultraviolet Absorbents

Alumisalicylate, menthyl salicylate, homomenthyl salicylate, octyl salicylate, phenyl salicylate, benzyl salicylate, p-isopropanol phenyl salicylate, dipropylene glycol salicylate, etc.

(4) Cinnamic Acid Type Ultraviolet Absorbents

Isoferulic acid, ferulic acid, caffeic acid, ethyl-4-isopiopyl cinnamic acid, methyl-1,5-diisopropyl, propyl-p-methoxy cinnamic acid, isoamyl-p-methoxy cinnamic acid, octyl-p-methoxy cinnamic acid, 2-ethoxyethyl-p-methoxy cinnamic acid, cyclohexyl-p-methoxy cinnamic acid, ethyl-α-cyano-β-phenyl cinnamic acid, 2-ethylhexyl-α-cyano-β-phenyl cinnamic acid, glycermono-2-ethylhexanoyl-diparamethoxy cinnamic acid, etc.

(5) Benzophenone Type Ultraviolet Absorbents 2,4-Dihydroxy benzophenone, 2-hydroxy-4-methoxy benzophenone, 2-hydroxy-4-methoxy benzophenone sodium sulfonate, 2,4-dihydroxy benzophenone, 2,2'-dihydroxy-4-metholoxy benzophenone, 2,2-dimethoxy benzophenone sodium sulfonate, 4-phenyl benzophenone, 4-hydroxy-3-carboxy benzophenone, etc.

(6) Other Ultraviolet Absorbents

Urocanic acid, ethyl urocanate, 3-(4-methylbenzylidene) d,1-camphor, 2-(2-hydroxy-5-methylphenyl)benzotriazole, 2-2-hydroxy-5-methylbenzoxazol, 2,2'-hydroxy-5-methylphenyl benztriazole, 2-(2'-hydroxy-5-t-octylphenyl) benzotriazole, 4-methoxy-4'-t-butyl-dibenzoyl methane, etc.

Of the ultraviolet absorbents, those which are particularly used for cosmetic articles include 2-ethylhexyl paradimethyl aminobenzoate (produced by VAN DYK Corp., "ESCALOL 507"), the mixture of para-methoxy cinnamic acid with 2,4-diisopropyl methyl cinnamale (produced by HARMAN-RAIMA Corp., "NEO HELIOPAN H & R"), methoxy octyl cinnamate (produced by HARMANRAIMA Corp., "NEO HELIOPAN AV"), 4-tert-butyl-4'-methoxy-dibenzoyl methane (produced by GIVAUDAN-ROURE Corp., "PARSOL 1789"), oxobenzone (produced by SIPURO Corp., "SISORUBU 101"), and 2-hydroxy-4-methoxy benzophenone-5-sulfonic acid (produced by SIPURO Corp., "SISORUBU 101S"), for example. Preferably, at least one member selected from the group of ultraviolet absorbents enumerated above is used.

The cosmetic article of this invention can contain the ultraviolet absorbent in an amount in the range of 0.001–20% by weight, preferably 0.01–10% by weight, based on the total weight of the cosmetic article. If the content of the ultraviolet absorbent is less than 0.001% by weight, the cosmetic article will tend to suffer an inability to obtain the effect of the combined use of the ultraviolet absorbent and the dispersion of the moisture-retaining agent. If this content exceeds 20% by weight, the excess will produce no proportionate addition to the effect and will do no good economically and the cosmetic article will prominently irk the user in the application thereof to the skin, particularly while spreading it into a uniform film, and suffer the ultraviolet absorbent contained therein to manifest an objectionable touch and particularly a feeling of ropiness.

Even when the dispersion of the moisture-retaining agent of this invention and the ultraviolet absorbent mentioned above are incorporated together in the cosmetic article, the cosmetic article allows this incorporation to proceed stably and acquires a high value of SPF and a high value of PFA because it shows no sign of crystallization of the ultraviolet absorbent, occurrence of a precipitate in a yellow to orange color due to the formation of a complex, or coloration of the cosmetic article.

This invention does not discriminate the cosmetic article on account of the kind thereof. The invention can be applied to foundations, for example. The cosmetic article is preferred to be intended for use on parts of the user's body which have as large areas as possible. As concrete examples of the form of the cosmetic article, lotions, emulsions, creams, and emulsifiable foundations may be cited.

EXAMPLES

Now, this invention will be described more specifically below with reference to working examples. It should be noted that this invention is not limited in any sense by these working examples. The mixing ratios mentioned in the working examples are invariably expressed in parts by weight.

Example 1

O/W Type Emulsion

| (Oil phase A) | |
|---|---|
| Beeswax | 0.35 |
| Spermaceti wax | 0.70 |

-continued

| | |
|---|---|
| Tri(lauryl, myristin, palmitin, stearic acid) glyceride | 0.70 |
| Sucrose fatty acid ester | 1.78 |
| Olive oil | 0.70 |
| Hazelnut oil | 0.70 |
| Tocopherol | 0.01 |
| Tri-2-ethylhexane glycerin | 0.04 |
| Stearic acid | 0.70 |
| Glycerin monostearate | 1.79 |
| Sorbitan trioleate | 0.77 |
| Glycerin monooleate | 0.77 |
| Dimethyl siloxane.methyl (polyoxyethylene) siloxane copolymer | 0.70 |
| Polyoxyethylene phytostanol | 0.88 |
| Methylparaben | 0.14 |
| (Dispersion of moisture-retaining agent B) | |
| Dispersion of moisture-retaining agent (TiO$_2$:ZnO = 1:2) | 35.08 |
| Purified water | 0.20 |
| (Neutral solution C) | |
| Potassium hydroxide | 0.14 |
| Purified water | 43.85 |

The film obtained by spreading on a surface the dispersion of the moisture-retaining agent in this example at a ratio of 0.03 g/40 cm$^2$ was found to have 36.5 as the value of SPF and 23.3 as the value of PFA. The concentrations of TiO$_2$ and ZnO in the dispersion of the moisture-retaining agent (the concentrations in the emulsion) were each 10% by weight. The gravimetric ratio of the inorganic ultraviolet intercepting material (superfine titanium dioxide particles and minute zinc oxide particles):dispersant (bentonite):moisture-retaining agent (propylene glycol) in the dispersion of the moisture-retaining agent was 1:0.4:2.1. The value of SPF and the value of PFA were determined by the following methods (similar hereinafter).

Method of Manufacture

The oil phase A was heated to 80° C. The dispersion of the moisture-retaining agent heated in advance to 80° C. was added to the hot oil phase A to effect crude emulsification. Then, the neutral solution C heated in advance to 80° C. was added to the crude emulsion to effect further emulsification. The resultant emulsion was cooled to 30° C. to obtain an O/W type emulsion having the oil phase O dispersed in the water phase W. The film obtained by spreading this emulsion on a surface at a ratio of 0.08 g/40 cm$^2$ was found to have 45.7 as the value of SPF and 25.8 as the value of PFA.

Example 2

W/O Type Emulsion

| | |
|---|---|
| (Oil phase A) | |
| Decamethyl cyclopentasiloxane | 11.0 |
| Octamethyl cyclotetrasiloxane solution containing 10% by weight of oxyethylene.oxypropylene copolymer | 21.0 |
| Dimethyl polysiloxane | 1.0 |
| Polyoxyethylene lauryl ether | 0.2 |
| Butyl paraben | 0.25 |
| Sorbitan monopalmitate | 2.0 |
| (Water phase B) | |
| Common salt | 2.0 |
| Sodium dehydroacetate | 0.2 |
| Methyl paraben | 0.2 |
| Dispersion of moisture-retaining agent | 45.0 |
| Purified water | 17.15 |

The film obtained by spreading on a surface the dispersion of the moisture-retaining agent in this example at a ratio of 0.03 g/40 cm$^2$ was found to have 47.0 as the value of SPF and 25.9 as the value of PFA. The concentration of TiO$_2$ in the dispersion of the moisture-retaining agent (the concentration in the emulsion) was 10% by weight. The gravimetric ratio of the inorganic ultraviolet intercepting material (superfine titanium dioxide particles):fixating agent (talc):dispersant (LAPONITE):moisture-retaining agent (1,3-butylene glycol) in the dispersion of the moisture-retaining agent was 1:0.4:0.3:2.8.

The oil phase A was heated to 50° C. The water phase B heated separately to 50° C. was added to the hot oil phase A to effect emulsification. The emulsion was cooled to 30° C. to obtain a W/O type emulsion. The film obtained by spreading the emulsion at a ratio of 0.08 g/40 cm$^2$ was found to have 25.3 as the value of SPF and 13.5 as the value of PFA.

Example 3

Carmine Lotion

| | |
|---|---|
| (A solution) | |
| Purified water | 44.71 |
| Dispersion of moisture-retaining agent | 8.8 |
| Common salt | 0.2 |
| (B solution) | |
| Ethyl alcohol | 9.0 |
| Menthol | 0.005 |
| Camphor | 0.025 |
| Methyl paraben | 0.25 |
| 2-Ethylhexyl paradimethyl aminobenzoate | 0.01 |
| (C solution) | |
| Sorbitol | 1.0 |
| Polyethylene glycol | 0.5 |
| Purified water | 35.5 |

The film obtained by spreading on a surface the dispersion of the moisture-retaining agent in this example at a ratio of 0.03 g/40 cm$^2$ was found to have 25.8 as the value of SPF and 15.1 as the value of PFA. The concentration of ZnO in the dispersion of the moisture-retaining agent (the concentration in the carmine lotion) was 2.5% by weight. The gravimetric ratio of the inorganic ultraviolet intercepting material (minute zinc oxide particles):dispersant (VEEGUM F):moisture-retaining agent [propylene glycol and 1,3-butylene glycol (gravimetric ratio 1:1)] in the dispersion of the moisture-retaining agent was 1:0.2:2.32.

A carmine lotion was obtained by adding B solution to A solution and then adding C solution further thereto. The film obtained by spreading the carmine solution to a surface at a rate of 0.08 g/40 cm$^2$ was found to have 10.2 as the value of SPF and 5.1 as the value of PFA.

Example 4

Emulsion Type Cream Foundation

| | |
|---|---|
| (Oil phase A) | |
| Butyl paraben | 0.08 |
| Stearic acid | 1.36 |
| Glycerin monostearate | 2.33 |
| Polyethylene glycol monostearate | 0.39 |
| Polyoxy sorbitan monostearate | 1.17 |

-continued

| | |
|---|---|
| Tri-2-ethylhexane glycerin | 2.04 |
| Coloring pigment | 1.00 |
| (Water phase B) | |
| Dispersion of moisture-retaining agent (TiO$_2$:ZnO = 1:1) | 70.2 |
| Triethanol amine | 0.54 |
| Purified water | 20.5 |

The film obtained by spreading the dispersion of the moisture-retaining agent of this invention to a surface at a ratio of 0.03 g/40 cm$^2$ was found to have 21.6 as the value of SPF and 14.3 as the value of PFA. The total concentration of TiO$_2$ and ZnO in the dispersion of the moisture-retaining agent was 20% by weight. The gravimetric ratio of the inorganic ultraviolet intercepting material (superfine titanium dioxide particles and minute zinc oxide particles) :fixating agent [talc and sericite (gravimetric ratio 1:1)] :dispersant (saponite):moisture-retaining agent (dipropylene glycol) in the dispersion of the moisture-retaining agent was 1:0.4:0.6:3.0.

The oil phase A was dissolved and dispersed by heating to 85° C. The water phase B heated in advance to 85° C. was gradually added to the hot oil phase A thereby effecting emulsification. The emulsion type cream foundation consequently obtained was cooled to 30° C. and spread on a surface at a ratio of 0.08 g/40 cm$^2$ to form a film. This film was found to have 40.3 as the value of SPF and 31.8 as the value of PFA.

Comparative Example 1

An emulsion was obtained by following the procedure of Example 1 while changing the components (minute zinc oxide, superfine titanium dioxide, moisture-retaining agent, and fixating agent) of the dispersion of the moisture-retaining agent of Example 1 to other composition mixture not conforming to the dispersion of this invention. This emulsion was found to have 16.1 as the value of SPF and 11.8 as the value of PFA.

Comparative Example 2

An emulsion was obtained similarly to Comparative Example 1 by following the procedure of Example 2 while changing the components of the dispersion of the moisture-retaining agent of Example 2 to other composition mixture not conforming to the dispersion of this invention. The emulsion (containing the superfine TiO$_2$ particles in a concentration of 5% by weight) was found to have 8.9 as the value of SPF and 6.9 as the value of PFA.

Comparative Example 3

An emulsion was obtained similarly to Comparative Example 1 by following the procedure of Example 3 while changing the components of the dispersion of the moisture-retaining agent of Example 3 to other composition mixture not conforming to the dispersion of this invention. The emulsion was found to have 5.1 as the value of SPF and 3.8 as the value of PFA.

Comparative Example 4

An emulsion was obtained similarly to Comparative Example 1 by following the procedure of Example 4 while changing the components of the dispersion of the moisture-retaining agent of Example 4 to other composition mixture not conforming to the dispersion of this invention. The emulsion was found to have 21.6 as the value of SPF and 15.0 as the value of PFA.

Example 5

O/W Type Emulsion

| | |
|---|---|
| (Oil phase A) | |
| Squalane | 4.0 |
| Olive Oil | 5.5 |
| Purified jojoba oil | 1.5 |
| Stearyl alcohol | 0.6 |
| d-δ-Tocopherol | 0.02 |
| Polyoxyethylene behenyl ether | 1.6 |
| Glyceryl monostearate | 0.5 |
| Glyceryl monooleate | 0.2 |
| (Dispersion of moisture-retaining agent B) | |
| Dispersion of moisture-retaining agent (TiO$_2$:ZnO = 1:2) | 22.2 |
| Carboxy vinyl polymer | 0.05 |
| Purified water | 31.9 |
| (Neutral solution C) | |
| Potassium hydroxide | 0.09 |
| Purified water | 31.84 |

The dispersion of the moisture-retaining agent in this example was composed of 45% by weight of an inorganic ultraviolet intercepting material (superfine titanium dioxide particles and minute zinc oxide particles) and 55% by weight of 1,3-butylene glycol. The film obtained by spreading this dispersion on a surface at a ratio of 0.03 g/40 cm$^2$ was found to have 38.7 as the value of SPF and 25.6 as the value of PFA. The total concentration (concentration in the emulsion) of TiO$_2$ and ZnO in the moisture-retaining agent was 10% by weight. This dispersion of the moisture-retaining agent was manufactured by following the procedure of Production Example 4 which will be cited herein below.

Method of Manufacture

The oil phase A was heated to 80° C. The dispersion of moisture-retaining agent B heated in advance to 80° C. was added to the hot oil phase A to effect crude emulsification. Then, the neutral solution C heated in advance to 80° C. was added to the crude emulsion to effect further emulsification. The emulsion was cooled to 30° C. to obtain an O/W type emulsion having the oil phase O dispersed in the water phase W. The film obtained by spreading this emulsion on a surface at a ratio of 0.08 g/40 cm$^2$ was found to have 48.9 as the value of SPF and 26.9 as the value of PFA.

Example 6

W/O Type Emulsion

| | |
|---|---|
| (Oil phase A) | |
| Decamethyl cyclopentasiloxane | 11.0 |
| Octamethyl cyclotetrasiloxane solution containing 10% by weight of oxyethylene.oxypropylene copolymer | 21.0 |
| Dimethyl polysiloxane | 1.0 |
| Polyoxyethylene lauryl ether | 0.2 |
| Butyl paraben | 0.25 |
| (Water phase B) | |
| Magnesium sulfate | 2.0 |
| Sodium dehydroacetate | 0.2 |

-continued

| | |
|---|---|
| Methyl paraben | 0.2 |
| Dispersion of moisture-retaining agent | 12.5 |
| Purified water | 51.65 |

The oil phase A was heated to 50° C. The water phase B separately heated in advance to 50° C. was added to the hot oil phase A to effect emulsification. The emulsion was cooled to 30° C. to obtain a W/O type emulsion. The film obtained by spreading this emulsion on a surface at a ratio of 0.08 g/40 cm² was found to have 26.4 as the value of SPF and 14.7 as the value of PFA.

The dispersion of the moisture-retaining agent in this example was composed of 40% by weight of the inorganic ultraviolet intercepting material (superfine titanium dioxide particles and minute zinc oxide particles) and 60% by weight of propylene glycol. The total concentration (concentration in the emulsion) of the superfine titanium dioxide particles and the minute zinc oxide particles in the moisture-retaining agent was 5% by weight. This dispersion of the moisture-retaining agent was manufactured by following the procedure of Production Example 4 which will be cited herein below.

Example 7

Carmine Lotion

| | |
|---|---|
| (A solution) | |
| Purified water | 44.71 |
| Dispersion of moisture-retaining agent | 8.33 |
| Common salt | 0.2 |
| (B solution) | |
| Ethyl alcohol | 9.0 |
| Menthol | 0.005 |
| Camphor | 0.025 |
| Methyl paraben | 0.25 |
| 2-Ethylhexyl paradimethyl aminobenzoate | 0.01 |
| (C solution) | |
| Sorbitol | 1.0 |
| Polyethylene glycol | 0.5 |
| Purified water | 35.97 |

The dispersion of the moisture-retaining agent in this example was composed of 30% by weight of the inorganic ultraviolet intercepting material (minute zinc oxide particles) and 70% by weight of glycerin. The film obtained by spreading this dispersion on a surface at a ratio of 0.03 g/40 cm² was found to have 28.8 as the value of SPF and 17.3 as the value of PFA. The concentration (concentration in the carmine lotion) of ZnO in the moisture-retaining agent was 2.5% by weight. This dispersion of the moisture-retaining agent was manufactured by following the procedure of Production Example 3 which will be cited herein below.

A carmine lotion was obtained by adding the B solution to the A solution and then adding the C solution further thereto. The film obtained by spreading this carmine lotion on a surface at a ratio of 0.08 g/40 cm² was found to have 11.4 as the value of SPF and 6.2 as the value of PFA.

Example 8

Emulsion Type Cream Foundation

| | |
|---|---|
| (Oil phase A) | |
| Butyl paraben | 0.08 |
| Stearic acid | 1.36 |
| Glycerin monostearate | 2.33 |
| Polyethylene glycol monostearate | 0.39 |
| Polyoxysorbitan monostearate | 1.17 |
| Tri-2-ethylhexane glycerin | 2.04 |
| Coloring pigment | 1.00 |
| (Water phase B) | |
| Dispersion of moisture-retaining agent (TiO₂:ZnO = 1:1) | 70.2 |
| Triethanol amine | 0.54 |
| Purified water | 20.5 |

The dispersion of the moisture-retaining agent in this example was composed of 20% by weight of the inorganic ultraviolet intercepting material [superfine titanium dioxide particles and minute zinc oxide particles (gravimetric ratio of 1:1)] and 80% by weight of dipropylene glycol. The film obtained by spreading this dispersion on a surface at a ratio of 0.08 g/40 cm² was found to have 85.9 as the value of SPF and 78.3 as the value of PFA. The total concentration (concentration in the emulsion type cream foundation) of the superfine titanium dioxide particles and the minute zinc oxide particles was 14.0% by weight. This dispersion of the moisture-retaining agent was manufactured by the procedure of Production Example 4 which will be cited herein below.

The oil phase A was dissolved and dispersed by heating at 85° C. The water phase B heated in advance to 85° C. was gradually added to the hot oil phase A to effect emulsification. The emulsion was cooled to 30° C. to obtain an emulsion type cream foundation. The film obtained by spreading this emulsion type cream foundation on a surface at a ratio of 0.08 g/40 cm² was found to have 41.5 as the value of SPF and 32.8 as the value of PFA.

Comparative Example 5

An emulsion was obtained by following the procedure of Example 5 while changing the components (the minute zinc oxide particles, superfine titanium dioxide particles, and moisture-retaining agent) of the dispersion of the moisture-retaining agent of Example 5 to other composition mixture not conforming to this invention. The emulsion was found to have 15.4 as the value of SPF and 10.0 as the value of PFA.

Comparative Example 6

An emulsion was obtained, similarly to Comparative Example 5, by following the procedure of Example 6 while changing the components of the dispersion of the moisture-retaining agent of Example 6 to other composition mixture not conforming to this invention. The emulsion was found to have 7.9 as the value of SPF and 5.6 as the value of PFA.

Comparative Example 7

An emulsion was obtained, similarly to Comparative Example 5, by following the procedure of Example 7 while changing the components of the dispersion of the moisture-retaining agent of Example 7 to other composition mixture not conforming to this invention. The emulsion was found to have 5.0 as the value of SPF and 3.9 as the value of PFA.

Comparative Example 8

An emulsion was obtained, similarly to Comparative Example 5, by following the procedure of Example 8 while changing the components of the dispersion of the moisture-retaining agent of Example 8 to other composition mixture not conforming to this invention. The emulsion was found to have 20.4 as the value of SPF and 15.0 as the value of PFA.

Now, examples of production of the dispersion of the moisture-retaining agent will be cited below.

Production Example 1

A mixture of 59.6 g of superfine titanium dioxide particles having an average single particle diameter of 0.03–0.05 μm (produced by Ishihara Sangyo Kaisha K.K., "TTO-55A"), 19.4 g of minute zinc oxide particles having an average single particle diameter of 0.28 μm (produced by Sakai Chemical Ind., Co., Ltd.), 38 g of talc having an average single particle diameter of 8.0 μm (produced by Asada Seifun K.K., "JA46R"), 33.6 g of aluminum magnesium silicate (produced by VANDERVILT Co., Inc., "VEEGUM-F"), 5.2 g of magnesium silicate (produced by LAPORTE Industries Ltd., "LAPONITE XLS") and 11.6 g of bentonite (produced by Kunimine Industries Co., Ltd., "KUNIPIA-F") was stirred and pulverized homogeneously in a grinding device. The resultant powder was placed in a ball mill made of alumina and attrited and pulverized for 24 hours. The powder mixed, attrited, and pulverized as described above and 360 g of 1,3-butylene glycol (produced by Kyowa Hakko Kogyo Co., Ltd.) added thereto were together subjected to the treatments of mixing, attriting, and dispersing for 48 hours to obtain a dispersion of a moisture-retaining agent.

Production Example 2

A mixture of 140 g of superfine titanium dioxide particles having an average single particle diameter of 0.01–0.03 μm (produced by Ishihara Sangyo Kaisha Ltd., "TTO-S-1"), 38 g of sericite having an average single particle diameter of 4.8 μm (produced by Sanshin Mining Ind., Co., Ltd.), 38 g of talc having an average single particle diameter of 8.0 μm (produced by Hayashi Kasei K.K., "S Talc"), 20 g of aluminum magnesium silicate (produced by VANDERVILT Co., Inc., "VEEGUM-F"), 9.7 g of magnesium silicate (produced by LAPORTE Industries Ltd., "LAPONITE XLS"), and 23.5 g of smectite (produced by Kunimine Industries Co., Ltd., "SUMECTON") was stirred and pulverized with a grinding device. The powder and 360 g of propylene glycol added thereto were together dispersed uniformly and then passed three times through a ball mill (KOBALL Mill, produced by Shiko-PANTEC K.K.) to obtain a dispersion of a moisture-retaining agent.

Production Example 3

A dispersion of a moisture-retaining agent was obtained by placing 320 g of superfine titanium dioxide particles having an average single particle diameter of 0.04 μm (produced by Ishihara Sangyo Kaisha K.K., "TTO-55A") in a ball mill made of alumina, then placing 480 g of 1,3-butylene glycol therein, and treating them together in the ball mill for 72 hours to obtain a dispersion of a moisture-retaining agent.

Production Example 4

In 1,440 g of propylene glycol (produced by Asahi Denka Kogyo K.K.), 480 g of superfine titanium dioxide particles having an average single particle diameter of 0.01–0.03 μm (produced by Ishihara Sangyo Kaisha Ltd., "TTO-S-1") and 720 g of minute zinc oxide particles having an average particle diameter of 0.28 μm were dispersed. The resultant dispersion was passed four times through a ball mill (KOBALL Mill produced by Shinko PANTEC K.K.) to obtain a dispersion of a moisture-retaining agent.

To evaluate the dispersions of moisture-retaining agents used in Examples 1–4 and 5–8 mentioned above with respect to stability under the effect of aging, the relevant samples obtained immediately alter manufacture, those obtained after one year's standing outdoors at normal temperature, and those obtained after three months' standing at 40° C. were tested for the values of SPF and PFA and visually examined as to the degree of persistence. The observation of the persistence was conducted on the samples resulting from the outdoor standing at normal temperature six months and one year after the standing and on the samples resulting from the standing at 40° C. one month and three months after the standing. The results are shown in Table 1 and Table 3.

Concerning the cosmetic articles of Examples 1–4 and 5–8 and the emulsions of Comparative Examples 1–4 and 5–8, the relevant samples obtained immediately after manufacture, those obtained after one year's standing outdoors at normal temperature, and those obtained after three months' standing at 40° C. were tested for the values of SPF and PFA and visually examined as to the degree of persistence. The observation of the persistence was conducted on the samples resulting from the outdoor standing at normal temperature six months and one year after the standing and on the samples resulting from the standing at 40° C. one month and three months after the standing. The samples were also tested for tactile sensation on the skin. The results are shown in Table 2 and Table 4.

TABLE 1

Results of rating of dispersion of moisture-retaining agent after one year's standing outdoors at normal temperature and after three months' standing at 40° C.

| | | Value of SPF | | | Value of PFA | | | After standing at normal temperature | | After standing at 40° C. | |
|---|---|---|---|---|---|---|---|---|---|---|---|
| | | | After | | | | | | | | |
| Dispersion of | Amount | Directly after | one year's standing at | After three months' | Directly after | After one year's standing at | After three months' | | | | |
| moisture-retaining agent | applied mg/cm² | manu-facture | normal temperature | standing at 40° C. | manu-facture | normal temperature | standing at 40° C. | For six months | For one year | For one month | For three months |
| Dispersion of moisture-retaining agent used in Example 1 | 0.75 | 36.5 | 35.7 | 30.7 | 23.3 | 23.0 | 20.6 | ◎ | ◎ | ◎ | ◎ |
| | 2.0 | not less than 100 | not less than 100 | not less than 100 | not less than 100 | not less than 100 | not less than 100 | | | | |

TABLE 1-continued

Results of rating of dispersion of moisture-retaining agent after one year's standing outdoors at normal temperature and after three months' standing at 40° C.

| | | Value of SPF | | | Value of PFA | | | After standing at | | | |
| | | | After | | | | | normal temperature | | After standing at 40° C. | |
| Dispersion of | Amount | Directly after | one year's standing at | After three months' | Directly after | After one year's standing at | After three months' | | | | |
| moisture-retaining agent | applied mg/cm² | manu- facture | normal temperature | standing at 40° C. | manu- facture | normal temperature | standing at 40° C. | For six months | For one year | For one month | For three months |
| Dispersion of moisture-retaining agent used in Example 2 | 0.75 | 40.7 | 40.7 | 45.9 | 25.9 | 25.7 | 25.0 | ◉ | ◉ | ◉ | ◉ |
| | 2.0 | not less than 100 | not less than 100 | not less than 100 | 60.0 | 60.9 | 58.4 | | | | |
| Dispersion of moisture-retaining agent used in Example 3 | 0.75 | 25.8 | 25.8 | 25.6 | 15.1 | 15.5 | 15.4 | ◉ | ◉ | ◉ | ◉ |
| | 2.0 | not less than 100 | not less than 100 | not less than 100 | 73.2 | 79.0 | 75.2 | | | | |
| Dispersion of moisture-retaining agent used in Example 4 | 0.75 | 21.6 | 20.3 | 21.6 | 14.3 | 14.5 | 13.9 | ◉ | ◉ | ◉ | ◉ |
| | 2.0 | 83.7 | 83.0 | 82.1 | 75.5 | 74.3 | 73.6 | | | | |

The mark ◉ indicates absolute absence of a change in the state of persistence in the observation.

TABLE 3

Results of rating of dispersion of moisture-retaining agent after one year's standing outdoors at normal temperature and after three months' standing at 40° C.

| | | Value of SPF | | | Value of PFA | | | After standing at | | | |
| | | | After | | | | | normal temperature | | After standing at 40° C. | |
| Dispersion of | Amount | Directly after | one year's standing at | After three months' | Directly after | After one year's standing at | After three months' | | | | |
| moisture-retaining agent | applied mg/cm² | manu- facture | normal temperature | standing at 40° C. | manu- facture | normal temperature | standing at 40° C. | For six months | For one year | For one month | For three months |
| Dispersion of moisture-retaining agent used in Example 5 | 0.75 | 38.7 | 38.0 | 31.9 | 25.6 | 25.0 | 22.3 | ◉ | ◉ | ◉ | ◉ |
| | 2.0 | not less than 100 | not less than 100 | not less than 100 | not less than 100 | not less than 100 | not less than 100 | | | | |
| Dispersion of moisture-retaining agentused in Example 6 | 0.75 | 42.1 | 41.9 | 42.6 | 28.0 | 27.4 | 26.5 | ◉ | ◉ | ◉ | ◉ |
| | 2.0 | not less than 100 | not less than 100 | not less than 100 | 64.8 | 64.1 | 59.9 | | | | |
| Dispersion of moisture-retaining agent used in Example 7 | 0.75 | 28.8 | 28.6 | 27.9 | 17.3 | 17.4 | 17.0 | ◉ | ◉ | ◉ | ◉ |
| | 2.0 | not less than 100 | not less than 100 | not less than 100 | 76.4 | 77.1 | 75.5 | | | | |
| Dispersion of moisture-retaining agent used in Example 8 | 0.75 | 24.8 | 24.2 | 25.0 | 17.3 | 17.0 | 16.7 | ◉ | ◉ | ◉ | ◉ |
| | 2.0 | 85.9 | 84.5 | 83.5 | 78.5 | 78.1 | 77.6 | | | | |

The mark ◉ indicates absolute absence of a change in the state of persistence in the observation.

I is clearly noted from the results shown above that the dispersions of moisture-retaining agents according to this invention showed only sparing alteration in the state of persistence over long periods of time and showed very small changes in the values of SPF and PFA and proved excellent in dispersibility and stability.

TABLE 2

Results of rating of examples and comparative examples

| | Amount applied, mg/cm² | Value of SPF | | | Value of PFA | | |
|---|---|---|---|---|---|---|---|
| | | Directly after manufacture | After one year's standing at normal temperature | After three months' standing at 40° C. | Directly after manufacture | After one year's standing at normal temperature | After three months' standing at 40° C. |
| Example 1 | 2.0 | 47.5 | 47.0 | 46.7 | 25.8 | 25.0 | 24.4 |
| Comparative Example 1 | 2.0 | 16.1 | 10.0 | 7.5 | 11.8 | 7.1 | 5.0 |
| Example 2 | 2.0 | 25.3 | 25.4 | 25.0 | 13.5 | 13.5 | 13.0 |
| Comparative Example 2 | 2.0 | 8.9 | 7.0 | 4.9 | 6.9 | 4.2 | 3.0 |
| Example 3 | 2.0 | 10.2 | 10.0 | 10.1 | 5.1 | 4.9 | 5.0 |
| Comparative Example 3 | 2.0 | 5.1 | 4.0 | 2.3 | 3.8 | 2.0 | 1.4 |
| Example 4 | 2.0 | 40.3 | 39.7 | 39.0 | 31.8 | 30.7 | 31.0 |
| Comparative Example 4 | 2.0 | 21.6 | 14.1 | 12.0 | 15.0 | 9.4 | 6.5 |

| | After standing at normal temperature | | After standing at 40° C. | | Tactile sensation on the skin |
|---|---|---|---|---|---|
| | For six months | For one year | For one month | For three months | |
| Example 1 | ◎ | ◎ | ◎ | ◎ | 10 |
| Comparative Example 1 | Δ | Δ | X | X | 4 |
| Example 2 | ◎ | ◎ | ◎ | ◎ | 10 |
| Comparative Example 2 | Δ | Δ | X | X | 6 |
| Example 3 | ◎ | ◎ | ◎ | ◎ | 9 |
| Comparative Example 3 | Δ | X | X | X | 3 |
| Example 4 | ◎ | ◎ | ◎ | ◎ | 8 |
| Comparative Example 4 | Δ | Δ | X | X | 3 |

The tactile sensation on the skin was rated on a 10-point scale using numerals, 1 to 10, such that the degrees of elongation and adhesiveness and fastness of contact of a uniform film rose in accordance as the numerals grew in value.

TABLE 4

Results of rating of examples and comparative examples

| | Amount applied, mg/cm² | Value of SPF | | | Value of PFA | | |
|---|---|---|---|---|---|---|---|
| | | Directly after manufacture | After one year's standing at normal temperature | After three months' standing at 40° C. | Directly after manufacture | After one year's standing at normal temperature | After three months' standing at 40° C. |
| Example 5 | 2.0 | 48.9 | 48.0 | 47.7 | 26.9 | 25.4 | 25.0 |
| Comparative Example 5 | 2.0 | 15.4 | 9.8 | 9.0 | 10.0 | 6.7 | 5.0 |
| Example 6 | 2.0 | 26.4 | 26.0 | 25.1 | 14.7 | 13.8 | 13.5 |
| Comparative Example 6 | 2.0 | 7.9 | 6.0 | 4.0 | 5.6 | 4.1 | 3.0 |
| Example 7 | 2.0 | 11.4 | 11.6 | 11.0 | 6.2 | 4.3 | 4.1 |
| Comparative Example 7 | 2.0 | 5.0 | 4.0 | 2.2 | 3.9 | 2.1 | 2.0 |
| Example 8 | 2.0 | 41.5 | 40.7 | 40.9 | 32.8 | 31.5 | 31.0 |
| Comparative Example 8 | 2.0 | 20.4 | 13.6 | 11.2 | 15.0 | 9.2 | 6.1 |

| | After standing at normal temperature | | After standing at 40° C. | | Tactile sensation on the skin |
|---|---|---|---|---|---|
| | For six months | For one year | For one month | For three months | |
| Example 5 | ◎ | ◎ | ◎ | ◎ | 10 |
| Comparative Example 5 | Δ | Δ | X | X | 4 |

TABLE 4-continued

Results of rating of examples and comparative examples

| | | | | | |
|---|---|---|---|---|---|
| Example 6 | ⊙ | ⊙ | ⊙ | ⊙ | 10 |
| Comparative Example 6 | Δ | Δ | X | X | 6 |
| Example 7 | ⊙ | ⊙ | ⊙ | ⊙ | 9 |
| Comparative Example 7 | Δ | X | X | X | 3 |
| Example 8 | ⊙ | ⊙ | ⊙ | ⊙ | 8 |
| Comparative Example 8 | Δ | Δ | X | X | 3 |

The tactile sensation on the skin was rated on a 10-point scale using numerals, 1 to 10, such that the degrees of elongation and adhesiveness and fastness of contact of a uniform film rose in accordance as the numerals grew in value.

The results of the observation of the persistence were rated on a three-point scale, wherein ⊙ stands for absolute absence of alteration from immediately after manufacture onward, Δ for presence of fair agglomeration of particles and absence of separated particles, and × for prominent agglomeration of particles and presence of separated particles.

While the cosmetic articles of the examples conforming to this invention showed virtually no discernible change by aging in the values of SPF and PFA, those of the comparative examples showed degradations of the values of SPF and PFA due to the agglomeration of particles. The samples of Comparative Example 3 and Comparative Example 7 were observed to undergo gradual coloration due to aging.

Method for Determination of the Values of SPF and PFA

The values of SPF (sun protection factor) and PFA can be determined by the following procedure using an SPF analyzer (produced by Optometrics Corp., "SPF-290 Analyzer"). Thus, the values of SPF and PFA were determined by the following procedure.

(1) A transpore surgical tape made by 3M Co. is pasted to a quartz plate, 100 mm in length×100 mm in width×3 mm in height, and an area for application of a sample coat, 6.4 cm×6.4 cm (40 cm$^2$), is secured on the tape.

(2) A sample is applied with a sponge puff in two amounts, 0.03 g and 0.08 g (0.75 mg/cm$^2$ and 2.0 mg/cm$^2$), to the area secured on the tape and then left standing for 15 minutes.

(3) By the use of the SPF analyzer mentioned above, a measuring light having an irradiating area, 16 mm in diameter, is projected at nine spots on the surface coated with the sample to find nine measurements, which are averaged to obtain the values of SPF and PFA.

(4) This procedure, depending on the kind of sample, is repeated several times and the results severally obtained are averaged.

The dispersion of a moisture-retaining agent of the invention can manifest the following basic effects because it has dispersed in the moisture-retaining agent an inorganic ultraviolet intercepting material having the molecules of the moisture-retaining agent adsorbed thereon by a mechanochemical reaction.

(1) It allows the inorganic ultraviolet intercepting material to remain in a perfectly dispersed state for a long time.

(2) It permits repression of the optical activity and the catalytic activity of the inorganic ultraviolet intercepting material. It, therefore, is incapable of producing an adverse effect on the other components contained in the cosmetic article or agglomerating itself in combination with the other components. For example, it neither discolors or fades the tar substance legally accepted for use in cosmetic articles nor degenerates the standard oil agent for use in cosmetic articles. It does not agglomerate itself in combination with a thickening agent.

(3) It allows the cosmetic article incorporating it to impart a highly satisfactory tactile sensation to the skin and form a uniform film excelling in adhesiveness and spreadability on the skin.

(4) When it is used as incorporated in a cosmetic article, it emits a perfectly pleasing tactile sensation and forms on the skin a uniform film excelling in fastness of adhesion, expandability, etc.

(5) The cosmetic article incorporating it can be easily and conveniently manufactured. In the cosmetic article industry, the trend of lowering the production cost has been gaining in impetus and the conservation of labor in the production process of the cosmetic article has been constituting an important task. Since the effective protection of the skin against the ultraviolet light forms the basic need on the part of consumers, the need of the cosmetic article maker to procure a dispersion having such inorganic ultraviolet intercepting materials as superfine titanium dioxide particles, superfine zinc oxide particles, and minute zinc oxide particles incorporated as dispersed therein, namely the need to simplify the process of production by obtaining direct use of the dispersion instead of pulverizing the inorganic materials and dispersing the resultant powder, has been finding growing recognition. The dispersion of the moisture-retaining agent of this invention enables the maker of a cosmetic article to simplify the process of production by direct use of the dispersion of this invention instead of pulverizing and dispersing the powders of the inorganic ultraviolet intercepting materials. Further, the dispersion can be incorporated in the cosmetic article in a high concentration by a simple operation of dispersion.

The dispersion of a moisture-retaining agent of the invention manifests the basic effects mentioned above more advantageously.

The cosmetic article of the invention can manifest the following basic effects because it contain the dispersion of a moisture-retaining agent of the invention.

(1) It allows the inorganic ultraviolet intercepting material to remain in a perfectly dispersed state for a long time. As a result, it allows the ultraviolet intercepting function to be thoroughly manifested for a long time.

(2) It represses the optical activity and the catalytic activity of the inorganic ultraviolet intercepting material and, therefore, prevents this material from producing any adverse effect on the other components contained in the cosmetic article. For example, the tar pigment legally accepted for use in cosmetic articles is not discolored or faded and the standard oil agent for use in cosmetic articles is not degenerated. The thickening agent is not agglomerated in combination with the inorganic ultraviolet intercepting material.

(3) The cosmetic article imparts a fully satisfactory tactile sensation to the skin and produces a uniform film excelling in adhesiveness and spreadability on the skin.

What is claimed is:

1. A dispersion comprising an inorganic ultraviolet intercepting material dispersed in a moisture-retaining agent, wherein the molecules of said moisture-retaining agent are adsorbed on said inorganic ultraviolet intercepting material by a mechanochemical reaction.

2. The dispersion according to claim 1, which further comprises a dispersant capable of aiding in the dispersion of said inorganic ultraviolet intercepting material.

3. The dispersion according to claim 1 or claim 2, wherein said inorganic ultraviolet intercepting material is fixed on a fixing agent capable of fixing an inorganic ultraviolet intercepting material.

4. The dispersion according to claim 2, wherein the inorganic ultraviolet intercepting material, the dispersant and the moisture-retaining agent are present in the following gravimetric ratios:

| inorganic ultraviolet intercepting material | 1 |
|---|---|
| dispersant | 0.2–0.9 |
| moisture-retaining agent | 2–9.5, | wherein the range recited for the moisture-retaining agent includes the weight of the molecules of moisture-retaining agent adsorbed on the inorganic ultraviolet intercepting material.

5. The dispersion according to claim 3, wherein the inorganic ultraviolet intercepting material, the dispersant and the moisture-retaining agent are present in the following gravimetric ratios:

| inorganic ultraviolet intercepting material | 1 |
|---|---|
| fixing agent | 0.4–0.9 |
| dispersant | 0.2–0.6 |
| moisture-retaining agent | 2–9.5, | wherein the range recited for the moisture-retaining agent includes the weight of the molecules of moisture-retaining agent adsorbed on the inorganic ultraviolet intercepting material.

6. The dispersion according to claim 1 or claim 2, wherein the amount of said inorganic ultraviolet intercepting material is at least 9.5% by weight.

7. The dispersion according to claim 1, wherein the amount of said inorganic ultraviolet intercepting material is in the range of 20–50% by weight, and the amount of said moisture-retaining agent is in the range of 50–80% by weight, wherein the range recited for the moisture-retaining agent includes the weight of the molecules of moisture-retaining agent adsorbed on the inorganic ultraviolet intercepting material.

8. The dispersion according to claim 1, wherein said inorganic ultraviolet intercepting material is at least one member selected from the group consisting of titanium dioxide and zinc oxide, and said moisture-retaining agent is at least one member selected from the group consisting of humidity-retaining agents suitable for incorporation into cosmetic articles.

9. The dispersion according to claim 2, wherein said inorganic ultraviolet intercepting material is at least one member selected from the group consisting of titanium dioxide and zinc oxide, said moisture-retaining agent is at least one member selected from the group consisting of humidity-retaining agents suitable for incorporation into cosmetic articles, and said dispersant is at least one member selected from the group consisting of natural and synthetic silicates, and natural and synthetic clayish minerals belonging to the family of smectites.

10. The dispersion according to claim 3, wherein said inorganic ultraviolet intercepting material is at least one member selected from the group consisting of titanium dioxide and zinc oxide, said moisture-retaining agent is at least one member selected from the group consisting of humidity-retaining agents suitable for incorporation into cosmetic articles, said dispersant is at least one member selected from the group consisting of natural and synthetic silicates, and natural and synthetic clayish minerals belonging to the family of smectites, and said fixing agent is at least one member selected from the group consisting of the family of illites,the family of kaolins, and magnesium silicates.

11. A cosmetic article comprising 3.5–80% by weight of the dispersion of a moisture-retaining agent set forth in claim 1.

12. A cosmetic article comprising 3.5–80% by weight of the dispersion of a moisture-retaining agent set forth in claim 2.

13. A cosmetic article comprising 0.5–80% by weight of the dispersion of a moisture-retaining agent set forth in claim 7.

14. The dispersion according to claim 11, wherein said inorganic ultraviolet intercepting material is at least one member selected from the group consisting of titanium dioxide and zinc oxide, and said moisture-retaining agent is at least one member selected from the group consisting of humidity-retaining agents suitable for incorporation into cosmetic articles.

15. The cosmetic article according to claim 12, wherein said inorganic ultraviolet intercepting material is at least one member selected from the group consisting of titanium dioxide and zinc oxide, said moisture-retaining agent is at least one member selected from the group consisting of humidity-retaining agents suitable for incorporation into cosmetic articles, and said dispersant is at least one member selected from the group consisting of natural and synthetic silicates, and natural and synthetic clayish minerals belonging to the family of smectites.

* * * * *